(12) United States Patent
Nicholson et al.

(10) Patent No.: US 11,589,948 B2
(45) Date of Patent: Feb. 28, 2023

(54) HOOKED SURGERY CAMERA

(71) Applicant: Verb Surgical Inc., Santa Clara, CA (US)

(72) Inventors: Margaret F. Nicholson, Deptford, NJ (US); Berk Gonenc, Cupertino, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 522 days.

(21) Appl. No.: 16/723,778

(22) Filed: Dec. 20, 2019

(65) Prior Publication Data
US 2020/0205931 A1    Jul. 2, 2020

Related U.S. Application Data

(60) Provisional application No. 62/785,455, filed on Dec. 27, 2018.

(51) Int. Cl.
| | | |
|---|---|---|
| *B25J 9/18* | (2006.01) | |
| *A61B 90/00* | (2016.01) | |
| *A61B 34/10* | (2016.01) | |
| *A61B 34/35* | (2016.01) | |
| *A61B 34/00* | (2016.01) | |
| *A61B 34/37* | (2016.01) | |
| *A61B 34/30* | (2016.01) | |

(52) U.S. Cl.
CPC ............ *A61B 90/361* (2016.02); *A61B 34/10* (2016.02); *A61B 34/25* (2016.02); *A61B 34/35* (2016.02); *A61B 34/37* (2016.02); *A61B 2034/302* (2016.02); *A61B 2090/373* (2016.02); *A61B 2090/3991* (2016.02)

(58) Field of Classification Search
CPC ....... A61B 90/361; A61B 34/10; A61B 34/35; A61B 35/25; A61B 2034/302; A61B 34/37; A61B 2090/3991; A61B 2090/373; G05B 2219/45117; G05B 2219/45119
See application file for complete search history.

(56) References Cited

U.S. PATENT DOCUMENTS

2016/0345950 A1    12/2016    Scott

FOREIGN PATENT DOCUMENTS

| CN | 101610354 A | * | 12/2009 | |
| CN | 207477480 U | * | 6/2018 | ......... A61B 1/00016 |
| EP | 3628259 A1 | * | 4/2020 | ............. A61B 34/30 |

* cited by examiner

*Primary Examiner* — Karen Masih
(74) *Attorney, Agent, or Firm* — Womble Bond Dickinson (US) LLP

(57) ABSTRACT

A hooked surgery camera for use in surgical robotic systems includes a hook coupled to a side or end of a camera body, for attaching the camera to tissue during a surgery. The camera also includes a lens on another end of the camera body, and electronic components inside the camera body. The electronic components include a battery, a digital camera module and a wireless data transmitter. The hooked surgery camera provides a supplementary view of the surgical site, that is from a different perspective than the view provided by an endoscope, during laparoscopic surgeries. Other aspects are also described and claimed.

21 Claims, 5 Drawing Sheets

HOOKED SURGERY CAMERA

This non-provisional patent application claims the benefit of the earlier filing date of U.S. provisional patent application No. 62/785,455 filed Dec. 27, 2018.

TECHNICAL FIELD

The subject technology generally relates to surgical robotic systems and more specifically to wireless cameras suitable for capturing images of a surgical site inside a patient's body during minimally invasive surgeries.

BACKGROUND

Minimally invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more surgical tools (e.g., end effectors and endoscope) through the incisions into the patient. The surgical procedures may then be performed using the introduced surgical tools, with the visualization aid provided by the endoscope.

Generally, MIS provides multiple benefits, such as reduced patient scarring, less patient pain, shorter patient recovery periods, and lower medical treatment costs associated with patient recovery. Recent technology development in robotic systems allows more MIS to be performed with one or more robotic arms for manipulating surgical tools based on commands from a remote operator. A robotic arm may, for example, support at its distal end various devices such as surgical end effectors, imaging devices, cannulas for providing access to the patient's body cavity and organs, etc. In robotic MIS systems, it may be desirable to establish and maintain high positional accuracy for surgical instruments supported by the robotic arms.

Existing robotically assisted surgical systems usually consist of a surgeon console that resides in the same operating room as the patient and a patient-side cart with four interactive robotic arms controlled from the console. Three of the arms hold instruments such as scalpels, scissors, or graspers, while the fourth arm supports an endoscope. Surgeons today often rely on the view provided by the endoscope to manipulate tissues and perform surgical tasks. It is desirable to have more visual assistance during general or other laparoscopic surgeries.

SUMMARY

Disclosed herein is a hooked surgery camera for use in surgical robotic systems to provide supplementary visual assistance during laparoscopic, hybrid, or open surgical procedures. The hooked surgery cameras may be positioned around and within the surgical site to capture video or images of locations that are not visible to the endoscope. This additional visual assistance provided by one or more hooked surgery cameras may help surgeons avoid damaging tissues, nerves and vessels that are not visible in the endoscope view, save time on manipulating tissues for better visibility, and manage emergencies effectively.

Generally, the camera comprises a camera body, a hook coupled to a side or to a proximal end of the camera body operable to attach the camera to tissues during a surgery. The camera also comprises a camera lens on a distal end of the camera body, a transmitter in the camera body communicatively coupled to an external device, a digital camera module in the camera body configured to capture images and forward the images to the transmitter. A battery is also embedded in the camera body for providing power to the camera module and the transmitter.

In some variations, a string is coupled to the camera body or to the hook, and the string is also clamped to surgical drapes. A user pulling the string can retrieve the hooked camera. In some variations, the camera body (and optionally the lens) is sealed in a polycarbonate shell. In some variations, the proximal end of the camera body is bendable for adjusting an orientation of the field of the view of the camera. This bendable version of the proximal end may be active, in that it comprises a bending shell, one or more bending disks, and a motorized or powered actuator that performs the bending work. In some variations, the camera further comprises one or more light sources to illuminate its field of view. In some variations, the camera lens is a wide-angle lens, and the external device is a surgeon user console display on which an endoscope view is being displayed simultaneously with a view from the hooked camera.

The above summary does not include an exhaustive list of all aspects of the present disclosure. It is contemplated that the disclosure here includes all systems and methods that can be practiced from all suitable combinations of the various aspects summarized above, as well as those disclosed in the Detailed Description below and particularly pointed out in the Claims section. Such combinations may have particular advantages not specifically recited in the above summary.

BRIEF DESCRIPTION OF THE DRAWINGS

Several aspects of the disclosure here are illustrated by way of example and not by way of limitation in the figures of the accompanying drawings in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

DETAILED DESCRIPTION

Examples of various aspects and variations of the subject technology are described herein and illustrated in the accompanying drawings. The following description is not intended to limit the invention to these embodiments, but rather to enable a person skilled in the art to make and use this invention.

System Overview

A robotic-assisted surgical system (surgical robotic system) disclosed herein is a software-controlled, electro-mechanical system designed for surgeons to perform minimally invasive surgery. The surgical robotic system has an endoscope, compatible endoscopic instruments, and accessories. The system may be used by trained physicians in an operating room environment to assist in the accurate control of compatible endoscopic instruments during robotically assisted urologic, gynecologic and other laparoscopic surgical procedures. The system also allows the surgical staff to reposition the patient by adjusting the table without undocking the robotic arms during urologic, gynecologic and other laparoscopic surgical procedures. The compatible endoscopic instruments and accessories for use with the surgical system are intended for endoscopic manipulation of tissue including grasping, cutting, blunt and sharp dissection, approximation, ligation, electrocautery, and suturing.

Figure 1:
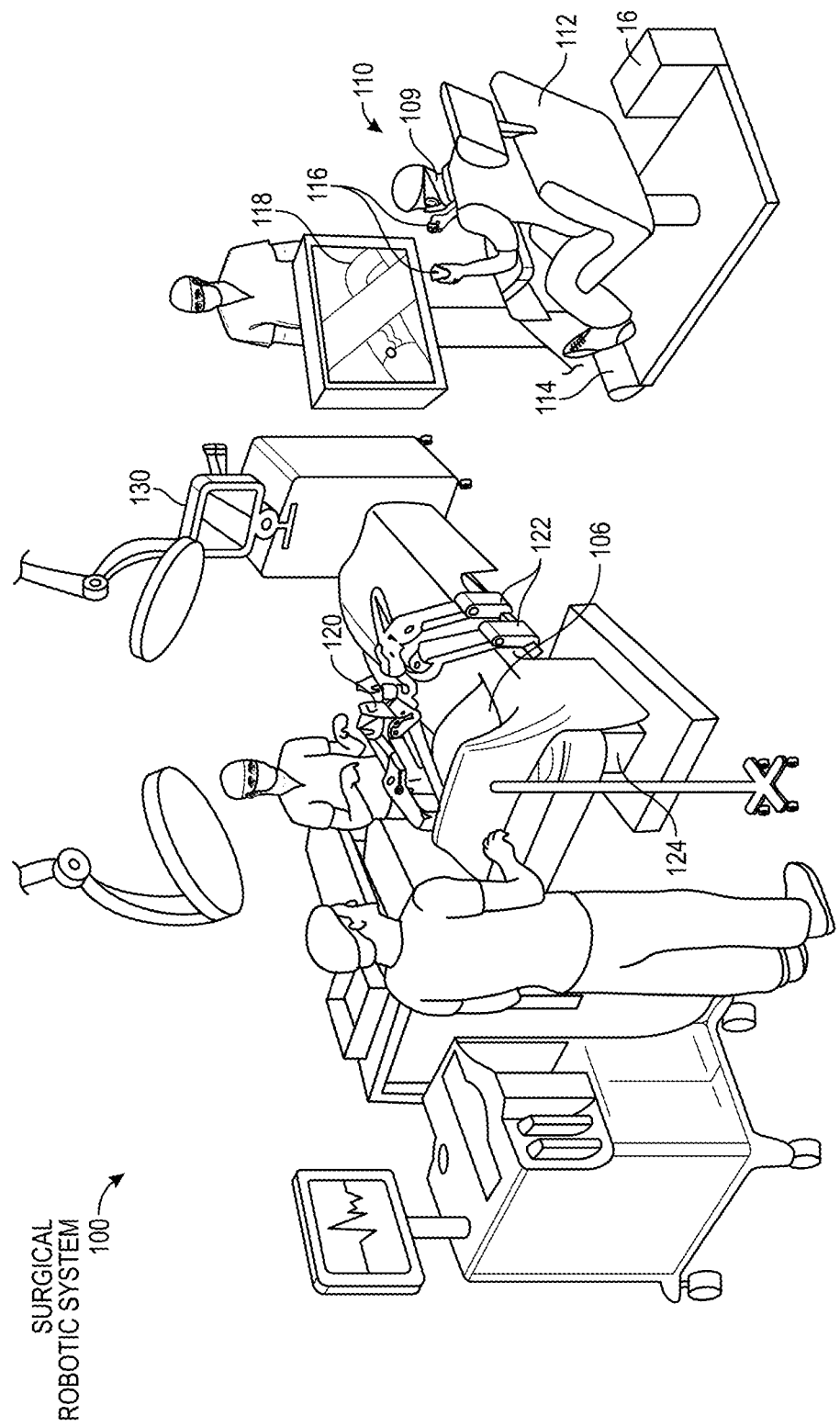
FIG. 1 is a diagram illustrating an example operating room environment with a surgical robotic system, in accordance with aspects of the subject technology.

FIG. 1 is a diagram illustrating an example operating room environment with a surgical robotic system 100, in accordance with aspects of the subject technology. As shown in FIG. 1, the surgical robotic system 100 comprises a user console 110, a control tower 130, and a surgical robot 120 having one or more surgical robotic arms 122 mounted on a surgical platform 124 (e.g., a table or a bed, etc.) where surgical tools referred to as end effectors are attached to the distal ends of the robotic arms 122 for executing a surgical procedure. The robotic arms 122 are shown as table-mounted (a patient 106 is lying on the table), but in other configurations the robotic arms may be mounted in a cart, a ceiling, a sidewall, or other suitable support surfaces.

Generally, a user 109, such as a surgeon or other operator, may be seated at the user console 110 to remotely manipulate the robotic arms 122 and surgical instruments (e.g., teleoperation). The user console 110 may be located in the same operation room as the robotic system 100, as shown in FIG. 1. In other environments, the user console 110 may be located in an adjacent or nearby room or tele-operated from a remote location in a different building, city, or country. The user console 110 may comprise a seat 112, pedals 114, one or more handheld user interface devices (UIDs) 116, and a console display 118 configured to display, for example, a view of the surgical site inside the patient 106. As shown in the exemplary user console 110, the user 109 (e.g., a surgeon) sitting in the seat 112 and viewing the console display 118 may manipulate the pedals 114 and/or the handheld UIDs 116 to remotely control the robotic arms 122 and more particularly the surgical instruments mounted to the distal ends of the arms 122 and whose tips are inside the body of the patient 106.

In some variations, a user may also operate the surgical robotic system 100 in an "over the bed" (OTB) mode, in which the user is at the patient's side and is simultaneously controlling a robotically-driven tool with a handheld UID 116 held in one hand and a manual laparoscopic tool with another hand. For example, the user's left hand may be manipulating a handheld user interface device 116 to control a robotic surgical component, while the user's right hand may be manipulating a manual laparoscopic tool. Thus, in these variations, the user may perform both robotic-assisted MIS and manual laparoscopic surgery on a patient.

During an exemplary procedure or surgery, the patient is prepped and draped in a sterile fashion to achieve anesthesia. Initial access to the surgical site may be performed manually, while the robotic system 100 is in a stowed configuration or withdrawn configuration to facilitate access to the surgical site. Once the manual access is completed, initial positioning and/or preparation of the robotic system may be performed. During teleoperation, a surgeon at the user console 110 may utilize the pedals 114 and/or user interface devices 116 to manipulate various end effectors and/or imaging systems to perform the surgery. Manual assistance may also be provided at the patient table by sterile-gowned personnel, who may perform tasks including but not limited to retracting tissues or performing manual repositioning or tool exchange involving one or more robotic arms 122. Non-sterile personnel may also be present to assist the surgeon at the user console 110. When the procedure or surgery is completed, the robotic system 100 and/or user console 110 may be configured or set in a state to facilitate one or more post-operative procedures, including but not limited to robotic system 100 cleaning and/or sterilisation, and/or healthcare record entry or output (electronic or hard copy) such as via the user console 110.

In some aspects, the communication between the surgical robot 120 and the user console 110 may be through the control tower 130, which may translate user input from the user console 110 into robotic control commands and transmit the control commands to the surgical robot 120. The control tower 130 may also transmit status and feedback from the robot 120 back to the user console 110. The data communication connections between the surgical robot 120, the user console 110 and the control tower 130 may be via wired and/or wireless connections, and may be proprietary and/or performed using any of a variety of data communication protocols. Any wired connections may be optionally built into the floor and/or walls or ceiling of the operating room. The surgical robotic system 100 may provide video output to one or more displays, including displays within the operating room, as well as remote displays accessible via the Internet or other networks. The video output or video feed may also be encrypted to ensure privacy and all or portions of the video output may be saved to a server or electronic healthcare record system.

Prior to initiating surgery using the surgical robotic system, the surgical team can perform a preoperative setup. During the preoperative setup, the main components of the surgical robotic system (table 124, robotic arms 122, control tower 130, and user console 110) are positioned in the operating room, connected with any needed cables, and powered on. The table 124 and robotic arms 122 may be in a fully-stowed configuration where the arms 122 are for example under the table 124 for storage and/or transportation purposes. The surgical team can extend the arms from their stowed position, for sterile draping of the arms. After draping, the arms 122 can be partially retracted until needed to be set up for teleoperation. A number of conventional laparoscopic steps may need to be performed including trocar placement into the patient's body, and insufflation. For example, the trocar can be inserted with the aid of an obturator, into a small incision and through the patient's body wall. Some sleeve and obturator assemblies also allow optical entry for visualization of tissue layers during insertion to minimize risk of injury during placement of the trocar. The endoscope is typically placed first into the patient's body (through a trocar that is in place), to provide hand-held camera visualization for placement of other trocars. After insufflation, if required, manual instruments can be inserted through the trocar to perform any laparoscopic steps by hand.

Next, the surgical team may position the robotic arms 122 over the patient and then dock (attach) each arm 122 to its corresponding trocar. Next, a surgical tool is inserted into the trocar and attached to each arm. The surgical robotic system 100 has the capability to uniquely identify each tool (endoscope and surgical instruments) as soon as it is attached to an arm. The system 100 will then display the tool type and arm location on the console display 118 at the user console 110, and on a touchscreen display at the control tower 130. The corresponding tool control functions are then enabled so that the tool can be manipulated robotically using inputs generated by the master UIDs 116 and foot pedals 114. A patient-side assistant can attach and detach a tool, as required, throughout the procedure. Once teleoperation mode has been enabled, the surgeon seated at the user console 110 can begin to perform surgery using the tools that are controlled by two master UIDs 116 (one in each hand of the surgeon) and by foot pedals 114. The system translates the surgeon's hand movements (e.g., wrist, fingers), via the master UIDs 116, into precise real-time movements of the surgical tools that essentially mimic those of the surgeon's hand. The system constantly monitors every maneuver of the surgeon, and pauses instrument movement if the system is unable to precisely mirror the surgeon's hand motions. In case the endoscope is moved from one arm to another during surgery, the system can adjust how it translates the spatial inputs of the master UIDs 116 to ensure instrument re-alignment and continued instrument control. The foot pedals 114 may be used to activate various system modes, such as endoscope control and various instrument functions including monopolar and bipolar cautery, without requiring the surgeon's hands to be removed from the master UIDs 116.

The table 124 can be repositioned intraoperatively. For safety reasons, all tool tips should remain in view and under active control by the surgeon at the user console 110. Instruments that are not under active surgeon control should be removed, and the table feet should be locked. During table motion, the integrated robotic arms 122 may passively follow the table movements. Audio and visual cues can be used to guide the surgery team during table motion. Audio cues may include tones and voice prompts. Visual messaging on the displays at the user console 110 and control tower 130 can inform the surgical team of the table motion status.

Graphic User Interface

Generally, a graphical user interface, GUI, for MIS systems may provide informative and/or interactive content, to thereby assist a user in performing a surgical procedure with one or more instruments. In some variations (e.g., in a surgical robotic system), a GUI is presented on a multi-panel display (or on multiple adjacent displays) through which content provided by various software apps may be overlaid or displayed next to images of the surgical site (e.g., from an endoscope and/or from a hooked surgery camera), such as during a surgical procedure. The software apps may be selectively arranged on the multiple panels to display their respective content in a reconfigurable manner. Different layouts of the reconfigurable panels may result from adjusting sizes and/or shapes of different panels. Additionally, or alternatively, different layouts may result from the population of different content (e.g., different apps) in the multiple display panels. In some variations, a GUI may further display one or more tool widgets configured to communicate information regarding surgical instruments, in a convenient, efficient manner. For example, tool widgets may summarize high-priority information such as tool type, tool state, tool settings, and/or tool "lives" remaining (e.g., number of firings left in a cartridge, etc.). Tool widgets may be overlaid over an endoscopic image, adjacent or proximate the endoscopic image, and/or in any other suitable portion of the displayed GUI.

Figure 2:
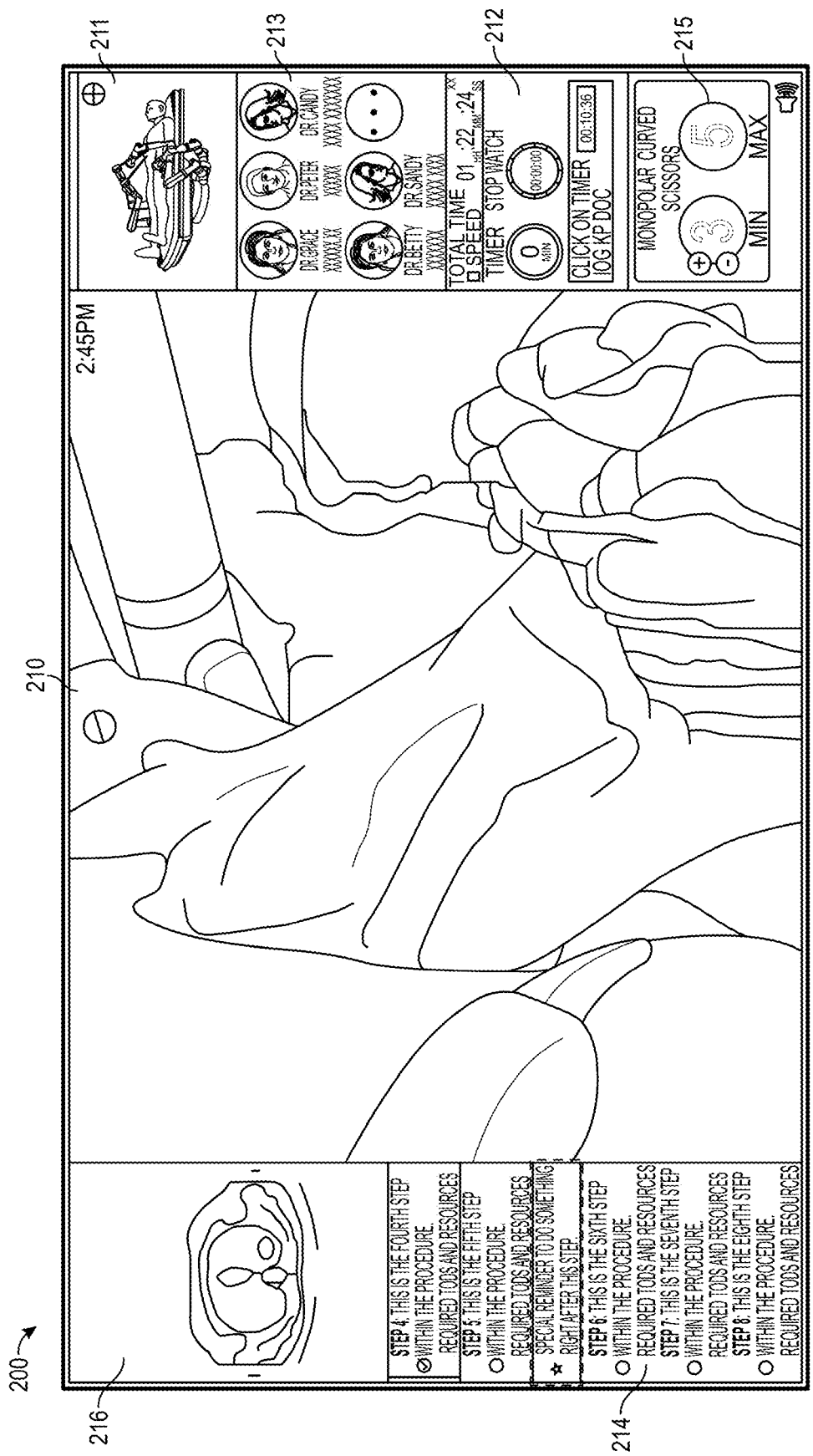
FIG. 2 is a diagram illustrating a screenshot of an exemplary graphical user interface, GUI, for a surgical robotic system during a robotic surgery, in accordance with aspects of the subject technology.

FIG. 2 is a diagram illustrating a screenshot 200 of an exemplary GUI for a surgical robotic system during a robotic surgery, in accordance with aspects of the subject technology. The screenshot 200 may be of the GUI as it is being displayed on the user console display 118—see FIG. 1. In the exemplary GUI, a video feed 210 of the surgical site is displayed in a main panel between two in this example vertical sidebars of the GUI. Various apps may be displayed in the sidebars on either side of the main panel, where at least some of the sidebar panels may be selectively hidden, minimized, made transparent, and/or pinned depending on the user's current preference. For example, a stadium view app 211, a timer app 212, a teleconferencing app 213, a procedure template/checklist app 214, a generator app 215, and a hooked camera view app 216 (discussed below), are displayed on the sidebars of the display. In addition, or alternatively, the GUI may be configured to display such specialized content (from one or more selected software apps) in the main panel.

The video feed 210 of the surgical site can be captured by an endoscope inserted into the body of the patient, also referred to here as an endoscope view. The endoscope can be manipulated (e.g., translation or rotation) manually or through a robot controller around an aperture or insertion point on the body wall to focus its view on different areas of the surgical site. In addition, the endoscope may also translate along the insertion axis to zoom in and out of the surgical site. However, the endoscope view of the surgical site is still constrained by the fixed point of insertion of the endoscope shaft (into the patient's body) and by the physical limitations of the camera that is at the tip of the endoscope (e.g., its field or angle of view). Only tissues or organs that are within the field of view (or also referred to here as "facing" the endoscope camera) can be seen on the display, provided they are not blocked by surgical instruments or by patient tissue that are also within the captured surgical site. Complementary views or views from different perspectives may be desirable, to assist the surgical process. An accessory camera referred to generally as a hooked surgery camera 300 and its view of the surgical site presented though a hooked camera view app 216 as described below, may provide such assistance.

Camera Design

Figure 3:
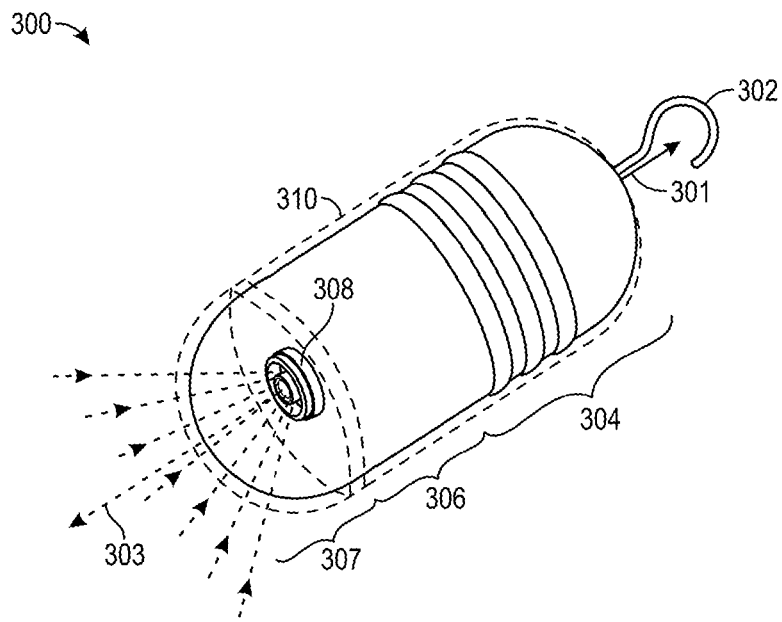
FIG. 3 is a diagram illustrating an exemplary design of a hooked capsule camera for use in MIS, in accordance with aspects of the subject technology.

FIG. 3 is a schematic diagram illustrating an exemplary design of the hooked capsule camera 300 for use in robotic surgery, in accordance with aspects of the subject technology. The exemplary hooked capsule camera comprises a hook 302, a camera body composed of a middle segment 306 and a rear segment 304, a digital camera module 308 that is enclosed within the body, and a lens 307. One end of the hook 302 is coupled to either a side of the body or, in the example shown, to a proximal end of the body (in the rear segment 304.) A curved, free end of the hook 302 can be used to attach the hooked surgery camera to patient tissue such as an abdominal wall during surgery on the patient. The lens 307 is positioned at a distal end of the body in front of the middle segment 306 as shown, and can be a wide angle optical lens, an indocyanine green (ICG) lens, or any other lenses suitable to surgical uses such as a fisheye lens that provides a wide field of view. The lens 307 may have one more lens elements, and a focal length of 20 mm or smaller that produces a full image frame captured by the digital camera module 308.

The hook 302 may be coupled to the proximal end, which is in the rear segment 304 of the body. In the example shown, the camera body is articulated or flexible to enable articulation between the hook and the portion of the body that is in front of the rear segment 304 (e.g., the lens 307.) The middle segment 306, which is directly adjacent the lens 307 at the front and directly adjacent the rear segment 304 at the rear, is said to be between the rear segment 304 and the lens 307. The middle segment 306 may house the digital camera module 308, one more lights, additional electronics and batteries. The additional electronics may include a data transmitter for wireless data transmission of the images captured by the digital camera module 308. The body of the hooked capsule camera and the lens 307 can together be sealed off as shown, e.g., hermetically, by a shell 310, such as one made of polycarbonate for sterilization and safety purposes.

As shown in the example of FIG. 3, the camera body is configured to be bendable into a bent position, for example by the user's hand, and holds the bent position when the user lets go of the camera 300. The bent position may be viewed as the angle alpha shown in FIG. 4 between an outward directed normal 301 and an imaging axis 303 of the camera module 308. See also FIG. 3 showing the outward directed normal 301 at the proximal end, and more specifically at the point where the hook is joined to the proximal end. The rear segment 304 of the body that includes the proximal end, to which the hook 302 is coupled, is bendable relative to the distal end at which there is the lens 207. This flexibility or articulation in the body can be achieved passively to achieve an effect similar to that exhibited by flexible gooseneck tubing, which enables the proximal end or the rear segment 304 to be bendable by a user's hand (e.g., while the user's other hand is holding the distal end fixed in place.) Once bent to the desired angle or position, the flexible structure maintains that position when the user lets go of the camera. For example, the rear segment can be passively bent after the hook is attached to the tissue, and the passive mechanism maintains its shape thereafter.

Figure 4:
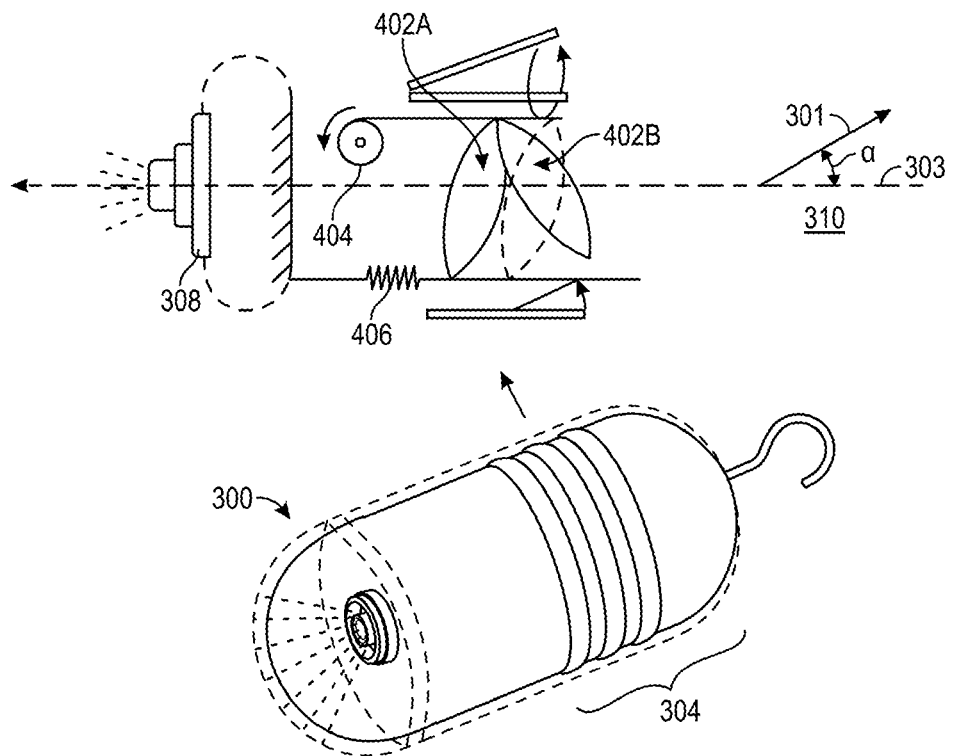
FIG. 4 is a diagram illustrating an exemplary articulation mechanism in a hooked capsule camera, in accordance with aspects of the subject technology.

In another design, the flexibility or articulation in the camera body may be remotely controlled using an active approach, where an actuator 404 or motorized mechanism (e.g., a snake-like bending mechanism) is signaled to bend the rear segment 304, by for example pulling a bending disk 402B as shown in FIG. 4 described below. In this way, the aim of the camera (the direction of the imaging axis through the lens 307) can exhibit different angles relative to the positioning of the hook on the tissue, making it easier to aim the camera at a surgical site of interest without having to re-orient how the hook is attached to the tissue. By contrast, in other implementations the body of the hooked capsule camera 300 can be a single rigid capsular in which case the orientation of the camera 300 can be adjusted by adjusting how the hook is attached to the tissue.

FIG. 4 is a schematic diagram illustrating an exemplary articulation mechanism in the hooked surgery camera 300, in accordance with aspects of the subject technology. In some implementations, the (flexible) rear segment 304 may house two or more disks with curved surfaces. For example, using two disks including one fixed disk 402A and one bending disk 402B enables the bending motion in at least one plane. The bending disk 402B may be driven by a cable-driven mechanism shown in the detail view at the top of FIG. 4, in which the actuator 404, e.g., a compact piezo electric actuator, pulls a cable that is attached to the bending disk 402B and thereby pivots the bending disk 402b (overcoming the tension in a pre-load spring 406), to bend the shell 310 by the angle alpha.

In some variations, one end of a string or a cable (not shown) is coupled to the body of the hooked capsule camera or to the hook 302, while another end of the string or the cable may be clamped to surgical drapes (not shown). In this manner, surgical staff pulling the string or the cable can easily retrieve the hooked capsule camera. A tracking mechanism, such as a radio frequency, RF, tracker or a magnetic tracker, can also be used for tracking and retrieving the hooked capsule camera (in addition to or in lieu of the string or cable.)

Use Cases

As described above, in a minimally-invasive surgery (MIS), such as a laparoscopic surgery or a robotic surgery, an image or video of a surgical site provides informative and/or interactive content to assist surgeons in performing the surgical procedure, as provided by the video feed 210 from an endoscope—see FIG. 2. However, because usually only a single endoscope is used to capture the surgical site in today's practice, surgeons often need to manipulate tissues to check surroundings and to identify targets and potential risks, which takes effort and intra-operative time. Indeed, this task of evaluating the surgical field can be continuous and repetitive throughout the operation, as dissection and manipulation alter the surgical landscape. It is desirable to have multiple views of the surgical site and/or means to observe the surgical site from different perspectives, so that surgeons can make better decisions and save time.

Figure 5:
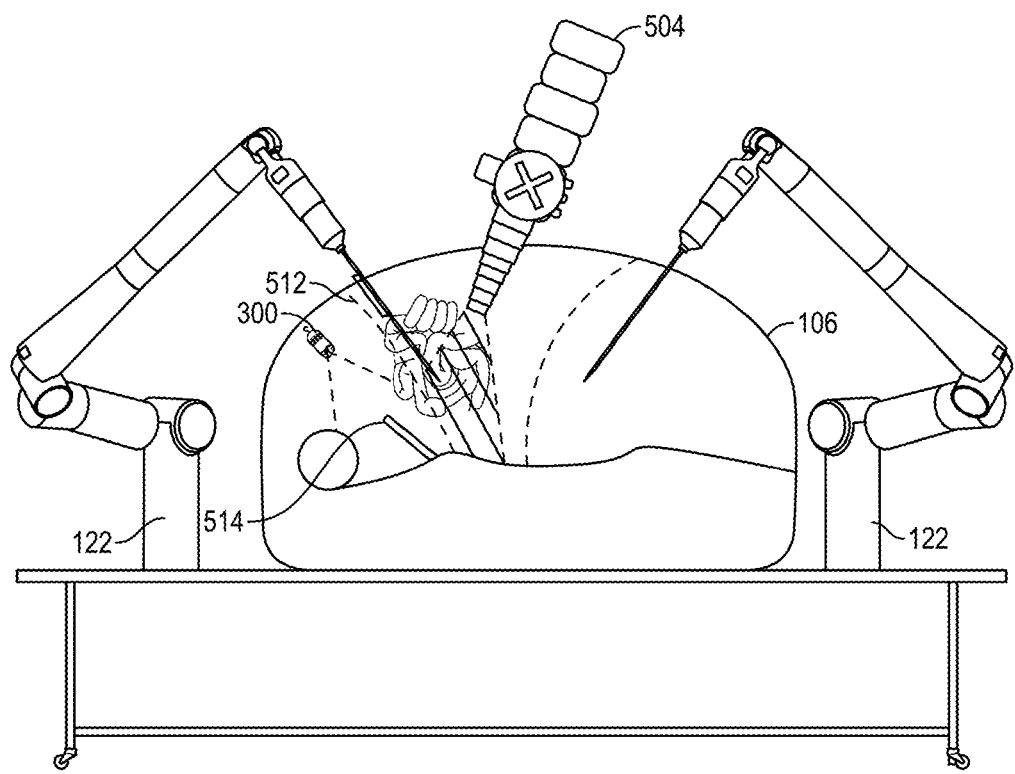
FIG. 5 is a diagram illustrating one example use case of the hooked capsule camera, in accordance with aspects of the subject technology.

The hooked surgery camera 300, as shown in FIG. 3 for example, may provide its view to a user via the hooked camera view app 216—see FIG. 2—that allows users including surgeons to see not only the surgical site that is facing the endoscope camera (displayed in the video feed 210), but also what is "around the corner" and therefore not visible in the video feed 210. Such one or more extra views that are displayed in the hooked camera view app 216 may enable surgeons to detect a critical nerve or blood vessel that may not be visible in the endoscope view (video feed 210) and therefore might be damaged by a surgical instrument. For example, when a surgeon uses a stapler, the hooked surgery camera can be attached to tissues opposite the direction that the stapler is approaching, to ensure that the surgeon can see the tips of the stapler and therefore only includes the structures to be stapled between the jaws of the stapler. Another example use case is illustrated in FIG. 5, which depicts the hooked surgery camera 300 placed behind an adhesions curtain 512. The adhesion curtain 512 blocks from the view of an endoscope 504 a blood vessel 514, i.e., the vessel 514 may not be visible in the images being captured by the endoscope (endoscope view) that is displayed to the surgeon, due to the adhesions curtain 512. In such a case, the surgeon can easily place the hooked surgery camera 300 behind the adhesions 512 where the field of view of the hooked surgery camera 300 captures the vessel 514 behind the curtain 512. These images captured by the camera 300 are displayed to the surgeon by the user console GUI (see FIG. 2) at the same time as the endoscope view, thereby enabling the surgeon to operate with a view of the vessel 514 and as a result avoid damage to the vessel 514.

Figure 6:
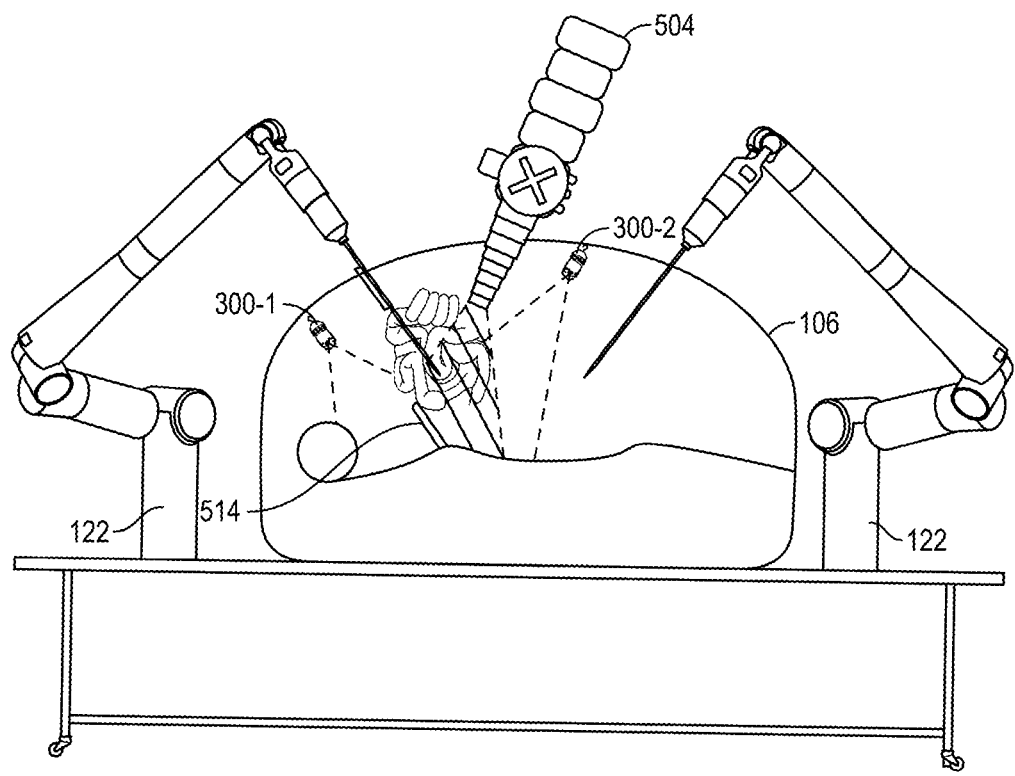
FIG. 6 is a diagram illustrating another example use case of the hooked capsule camera, in accordance with aspects of the subject technology.

FIG. 6 is a diagram illustrating another example use case of the hooked surgery camera 300, in accordance with aspects of the subject technology. During surgeries, bleeding (among other events) may occlude the endoscope lens, causing the surgeon to lose the entire view of the surgical site due to the presence of only one endoscope 504. When such occlusion happens, surgical tasks would be suspended while the endoscope is taken out of the patient, cleaned and reinserted into the body of the patient to regain the view. This process can cause delay and prevent the surgeon from stopping the bleeding promptly. With one or more hooked surgery cameras 300 placed around the surgical site, such as hooked surgery cameras 300A and 300B, the surgeon may switch to the views provided by the hooked surgery cameras 300A, 300B (in response to occlusion of the endoscope camera) and immediately plan and/or take actions to stop the bleeding, while watching the supplementary video/images captured by the hooked surgery cameras 300A, 300B and while waiting for the endoscope 504 to be cleaned and redeployed.

In addition to providing supplementary views, the use of multiple hooked surgery cameras may provide views from various perspectives, which can be combined to model a 3D mapping of the intracorporeal space. The views from multiple hooked surgery cameras can be further combined with the endoscope view to construct a better 3D view of the entire surgical site, which may lead to improved models for pre-operative planning and/or post-operative evaluations.

Figure 7:
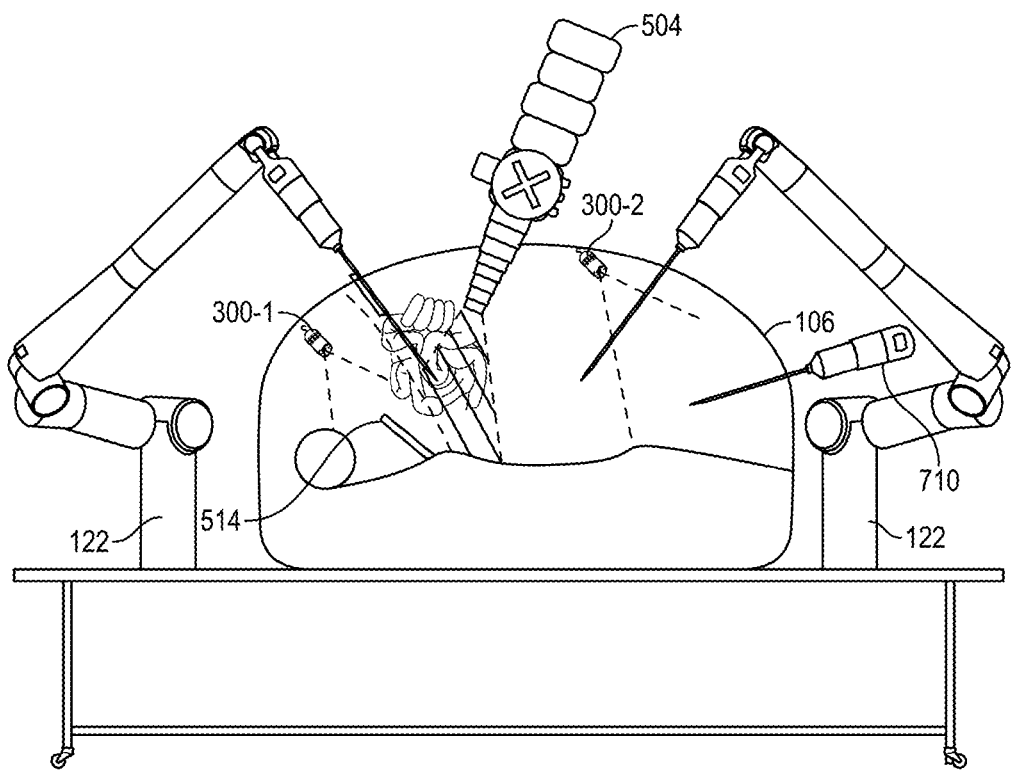
FIG. 7 is a diagram illustrating yet another example use case of the hooked capsule camera, in accordance with aspects of the subject technology.

FIG. 7 is a diagram illustrating yet another example use case of the hooked surgery camera 300, in accordance with aspects of the subject technology. In this example, several hooked surgery cameras are installed and are being used as accessory cameras at least one of which provides a view of an assistant port 710. In current practice, whenever surgical staff inserts a surgical instrument into the patient's body through a trocar port, the endoscope 504 needs to be directed or aimed toward that port. In some cases, during an ongoing surgery the surgical staff may have to insert a further instrument through what is referred to as an assistant port 710. Typically, the endoscope 504 must now be aimed at the assistant port 710, and therefore away from the surgical target, to provide the surgeon a visual on insertion of the new instrument (to ensure that the new instrument does not damage any tissue upon entry.) This process may divert the endoscope from ongoing surgical tasks at the surgical target, which normally causes a pause in the operation. It is beneficial in such a situation to have one or more hooked surgery cameras 300 attached to tissues around the surgical site, where the staff may now maneuver one of the hooked surgery cameras until it shows a view of the assistant port 710; the endoscope 504 may remain focused on the surgical target while the surgical staff is inserting the instrument into the assistant port 710 without disrupting the ongoing surgery.

Figure 8:
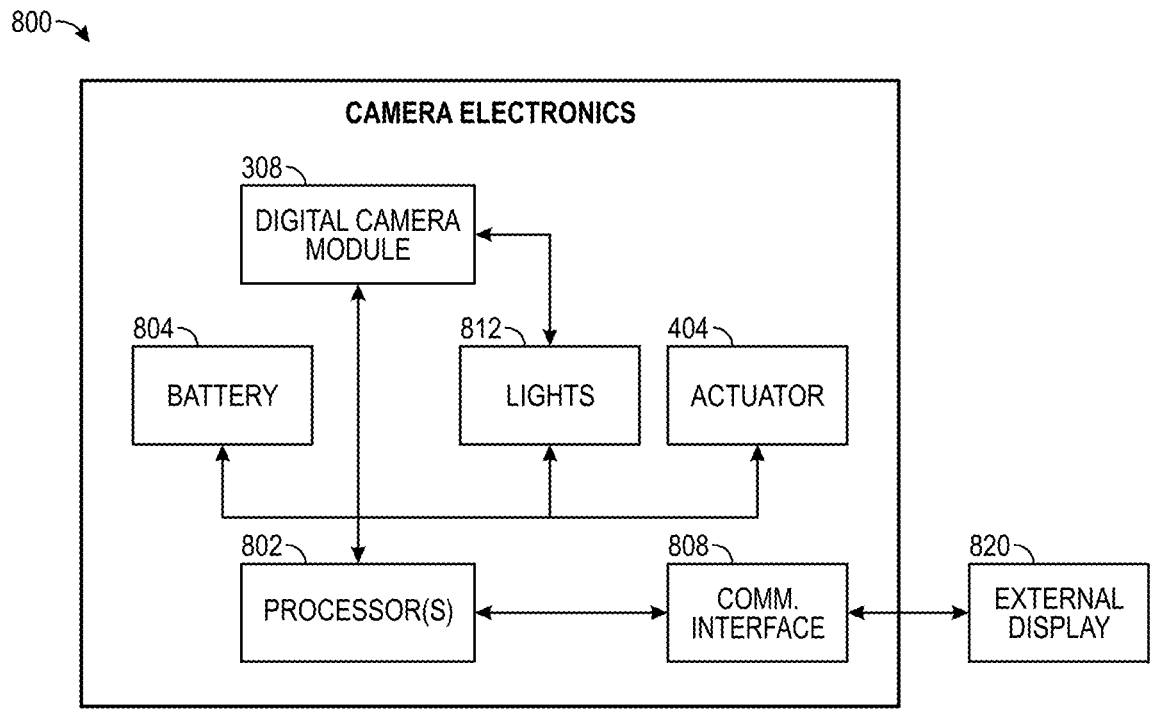
FIG. 8 is a block diagram illustrating exemplary electronic components of a hooked capsule camera, in accordance with aspects of the subject technology.

FIG. 8 is a block diagram illustrating an example of the electronic components in the hooked surgery camera 300, in accordance with aspects of the subject technology. The electronic components are referred to here as camera electronics 800 and may include the digital camera module 308, one or more lights 812 (e.g., LED light sources) to illuminate a field of view of the camera module 308, an actuator 404 used for bending the shell (in the case of an active flexible rear segment), one or more microelectronic processors 802 for managing various aspects of the camera 300 including the data communication interface 808, the camera module 398, the lights and the actuators, and a battery 804 for powering the various elements of the camera electronics 800. The processor 802 may also manage the power usage of the hooked surgery camera by turning on or off the power from the battery 804 to the actuator 404, the data communication interface 808, the digital camera module 308, and the lights 812. In some implementations, the camera module 308 may also directly activate or deactivate the lights 812.

The processors 802 may execute software stored in memory (not shown but considered to be part of the camera electronics 800) to process video (image sequence) captured by the digital camera module 308 and to prepare to send the video to the communication interface 808. The communication interface can be a wired or wireless network interface for transmitting the video to an external display 820 (e.g., the user console display 118—see FIG. 1.) The actuator 404 may be included to automatically drive a flexible segment (e.g., the rear segment 304) of the camera body for articulating the camera.

The foregoing description, for purposes of explanation, used specific nomenclature to provide a thorough understanding of the invention. However, it will be apparent to one skilled in the art that specific details are not required in order to practice the invention. For example, while FIG. 3 and FIG. 4 illustrate the camera body and the camera lens forming a capsule, where the distal end is one end of the capsule and the proximal end is another end, the overall shape does not have to be an exact cylinder with hemispherical ends. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications. They thereby enable others skilled in the art to best utilize the invention and various embodiments with various modifications as are suited to the particular use contemplated. It is intended that the following claims and their equivalents define the scope of the invention.

What is claimed is:

1. A hooked surgery camera for use as part of a surgical robotic system, the hooked surgery camera comprising:
   a camera body extending from a proximal end to a side and then to a distal end;
   a hook having one end coupled to the side or to the proximal end of the camera body, and another end to be attached to patient tissue;
   a camera lens mounted at the distal end of the camera body;
   a digital camera module in the camera body, the digital camera module configured to capture images through the camera lens;
   a wireless data transmitter in the camera body and communicatively coupled to the camera module to send the captured images to an external device;
   a light source in the camera body to illuminate a scene in a field of view of the camera lens; and
   a battery in the camera body to provide power to the transmitter and the digital camera module.

2. The camera of claim 1 further comprising a polycarbonate shell that seals off an outside surface of the camera body.

3. The camera of claim 1 wherein the hook is coupled to the proximal end and not the side of the camera body, and the camera body is configured to be bendable by a user's hand into a bent position and holds the bent position when the user lets go of the camera.

4. The camera of claim 1 wherein the hook is coupled to the proximal end and not the side of the camera body, and the camera body comprises a bending shell, one or more bending disks, and an actuator that can be signaled to pull the bending disk thereby forcing the bending shell into a bent position.

5. The camera of claim 1, wherein the camera lens has a focal length of 20 mm or smaller for a full frame camera module.

6. The camera of claim 1 wherein the external device is a surgical robotic system surgeon user console display.

7. The camera of claim 1 wherein the camera body and the camera lens form a capsule, the distal end being one end of the capsule and the proximal end being another end.

8. The camera of claim 1 further comprising a string coupled to the camera body or to the hook at one end, and to be clamped to a surgical drape at another end.

9. A hooked surgery camera for use as part of a surgical robotic system, the hooked surgery camera comprising:
 a camera body;
 a hook having one end coupled to the camera body, and another end to be attached to patient tissue;
 a camera lens mounted to the camera body, wherein the camera body and the camera lens form a capsule;
 a digital camera module in the camera body, the digital camera module configured to capture images through the camera lens;
 a wireless data transmitter in the camera body and communicatively coupled to the camera module to send the captured images to an external device; and
 a battery in the camera body to provide power to the wireless data transmitter and the digital camera module.

10. The camera of claim 9 wherein the camera body is configured to be bendable by a user's hand so that an angle between i) an outward directed normal at a location where the hook is joined to the camera body and ii) an imaging axis through the camera lens, can be changed into a bent position, and to hold the bent position when the user lets go of the camera.

11. The camera of claim 9 wherein the camera body comprises a bending shell, one or more bending disks, and an actuator that can be signaled to pull the bending disk thereby forcing the bending shell into a bent position.

12. The camera of claim 9, wherein the camera lens has a focal length of 20 mm or smaller for a full frame camera module.

13. The camera of claim 9 further comprising a light source in the camera body to illuminate a scene in a field of view of the camera.

14. The camera of claim 9 wherein the external device is a surgical robotic system surgeon user console display on which the captured images are being displayed at the same time as an endoscope view is being displayed.

15. A hooked surgery camera for use as part of a surgical robotic system, the hooked surgery camera comprising:
 a camera body;
 a hook having one end coupled to the camera body, and another end to be attached to a patient tissue;
 a camera lens mounted to the camera body;
 a digital camera module in the camera body, configured to capture images through the camera lens;
 a wireless data transmitter in the camera body and communicatively coupled to the camera module to send the captured images to an external device;
 a battery in the camera body to provide power to the wireless data transmitter and the digital camera module; and
 a string coupled to the camera body or to the hook at one end, and to be clamped to a surgical drape at another end.

16. A hooked surgery camera for use as part of a surgical robotic system, the hooked surgery camera comprising:
 a camera body;
 a hook having one end coupled to the camera body, and another end to be attached to a patient tissue;
 a camera lens mounted to the camera body;
 a digital camera module in the camera body, configured to capture images through the camera lens;
 a wireless data transmitter in the camera body and communicatively coupled to the camera module to send the captured images to an external device;
 a battery in the camera body to provide power to the wireless data transmitter and the digital camera module; and
 a shell that seals off the camera body and the camera lens.

17. A hooked surgery camera for use as part of a surgical robotic system, the hooked surgery camera comprising:
 a camera body;
 a hook having one end coupled to the camera body, and another end to be attached to patient tissue;
 a camera lens mounted to the camera body, wherein the camera lens is a wide-angle lens;
 a digital camera module in the camera body, the digital camera module configured to capture images through the camera lens;
 a wireless data transmitter in the camera body and communicatively coupled to the camera module to send the captured images to an external device; and
 a battery in the camera body to provide power to the wireless data transmitter and the digital camera module.

18. The camera of claim 17 wherein the wide-angle lens is a fisheye lens.

19. The camera of claim 17 wherein the wide-angle lens has a focal length of 20 millimeters or smaller that produces a full image frame captured by the digital camera module.

20. A hooked surgery camera for use as part of a surgical robotic system, the hooked surgery camera comprising:
 a camera body;
 a hook having one end coupled to the camera body, and another end to be attached to patient tissue;
 a camera lens mounted to the camera body;
 a digital camera module in the camera body, the digital camera module configured to capture images through the camera lens;
 a wireless data transmitter in the camera body and communicatively coupled to the camera module to send the captured images to an external device; and
 a battery in the camera body to provide power to the wireless data transmitter and the digital camera module, wherein the camera body is configured to be inserted into a patient's body through a trocar port.

21. The camera of claim 20 wherein the camera body is to be inserted into the patient's body and is to be maneuvered to show a view of an assistant port.

* * * * *